(12) United States Patent
Sikora

(10) Patent No.: US 7,020,239 B2  
(45) Date of Patent: Mar. 28, 2006

(54) METHOD AND DEVICE FOR THE DETERMINATION OF THE THICKNESS OF THE INSULATION OF A FLAT RIBBON CABLE IN THE REGION OF THE CONDUCTOR PATHS

(75) Inventor: Harald Sikora, Bremen (DE)

(73) Assignee: Sikora AG, Bremen (DE)

( * ) Notice: Subject to any disclaimer, the term of this patent is extended or adjusted under 35 U.S.C. 154(b) by 25 days.

(21) Appl. No.: 10/767,667

(22) Filed: Jan. 29, 2004

(65) Prior Publication Data

US 2004/0184575 A1  Sep. 23, 2004

(30) Foreign Application Priority Data

Feb. 21, 2003  (DE) ............................. 103 07 356

(51) Int. Cl.  
*G01B 15/02*  (2006.01)

(52) U.S. Cl. .......................... 378/50; 378/44
(58) Field of Classification Search ............... 378/50, 378/55, 44, 89

See application file for complete search history.

(56) References Cited

U.S. PATENT DOCUMENTS

| | | | | |
|---|---|---|---|---|
| 3,210,545 | A | * | 10/1965 | Barnett ........................ 250/308 |
| 3,796,874 | A | * | 3/1974 | Roller et al. ................... 378/54 |
| 4,129,778 | A | * | 12/1978 | Inoue et al. ................... 378/50 |
| 5,195,117 | A | * | 3/1993 | Ong ............................ 378/89 |

FOREIGN PATENT DOCUMENTS

| | | |
|---|---|---|
| DE | 27 47 638 | 6/1978 |
| DE | 100 19 789 | 4/2001 |
| DE | 199 50 254 | 5/2001 |
| DE | 100 34 747 A1 | 2/2002 |
| GB | 2 132 343 | 7/1984 |
| WO | 01/11316 | 2/2001 |

* cited by examiner

*Primary Examiner*—David V. Bruce  
*Assistant Examiner*—Hoon Song  
(74) *Attorney, Agent, or Firm*—Vidas, Arrett & Steinkraus, P.A.

(57) ABSTRACT

Method for the determination of the thickness of the insulation of a flat ribbon cable in the region of the metallic conductor paths, wherein one side of the flat ribbon cable is irradiated by means of an x-ray beam, and a detector on the same or on the opposing side of the flat ribbon cable measures the intensity of the x-ray luminescence radiation emitted by the respective conductor paths, the detector being shielded against the x-ray radiation.

23 Claims, 4 Drawing Sheets

METHOD AND DEVICE FOR THE DETERMINATION OF THE THICKNESS OF THE INSULATION OF A FLAT RIBBON CABLE IN THE REGION OF THE CONDUCTOR PATHS

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The invention is related to a method for the determination of the thickness of the insulation of a flat ribbon cable in the region of the conductor paths.

Flat ribbon cables are increasingly being used, particularly in the automotive industry. Flat ribbon cables present a plurality of strand-shaped flat conductor paths, which are disposed in a narrow distance side by side and which are embedded in insulation material. The width of the individual conductor paths varies according to the respective use, e.g. from 0.5 to 20 mm. The thickness of the conductor paths is approximately equal and is typically at 0.2 mm. The total thickness of the flat ribbon cable results from the thickness of the flat conductors and that of the insulations which are applied on both sides. A typical thickness of the insulation layers is 0.15 mm. Thus, the total thickness of the flat ribbon cable is about 0.5 mm.

Such flat ribbon cables have the advantage that an automatic assembly can take place with them, i.e. automatic bonding with other wires, plugs or the like. In order to do this, it is indispensable that the conductor paths have an accurate positioning inside the insulation envelope. For the user, however, it is also important to know whether the thicknesses of the insulation layers do have a predetermined value, particularly above and underneath the conductor paths.

Thus, the invention has the objective to state a method and a device for the determination of the thickness of the insulation of a flat ribbon cable in the region of the metallic conductor paths. Furthermore, a position determination of the conductor paths inside the insulation of the flat ribbon cable is intended to be possible with the aid of the method according to the invention.

BRIEF SUMMARY OF THE INVENTION

In the method according to the invention, one side of the flat ribbon cable is irradiated with an x-ray beam, and a detector is disposed on the same side of the flat ribbon cable and/or on the opposing side, which is sensitive for the x-ray luminescence radiation originating from the conductor path and which measures the intensity of the x-ray luminescence radiation. A shielding provides for that no primary x-ray radiation impinges on the detector.

Upon the more or less intense irradiation of the conductor paths of the flat ribbon cable with an x-ray radiation of medium energy, e.g. from 35 to 100 keV, a secondary radiation in a lower energy band is generated in the metallic conductor paths. This radiation is denoted as x-ray luminescence radiation. With copper conductors, it is essentially situated at 8 keV. The x-ray luminescence radiation penetrates through the insulation layer and is received by the detector. Even though the insulation layer is relatively thin, the secondary radiation experiences a significant attenuation. This attenuation is a measure for the wall thickness of the insulation and can be directly converted into a linear measure for the wall thickness, when the specific absorption values of the insulating material for the luminescence radiation are known.

With the aid of the described arrangement it is also possible to measure the differences between the conductor paths and the insulation. While the mentioned luminescence radiation originates from the conductor paths and is measured by the detector, no such secondary radiation can be detected in the region of mere insulation between the neighbouring conductor paths. Thus, with the described measuring method the lateral positions of the conductor paths can also be determined. In order to do this, there is also another possibility of evaluation, on which shall be dwelled on beneath.

Different arrangements are conceivable to accomplish the method according to the invention. One consists in keeping small the extension of the area of impingement of the x-ray beam on the flat ribbon cable transversely to the latter, in relation to the width of the conductor paths. Between the x-ray beam and the flat ribbon cable a relative movement is generated, through which the x-ray beam sweeps by and by the total width of the flat ribbon cable. The reception area of the detector is realised to be relatively large because of the relatively small intensity of the luminescence radiation. However, only that radiation which is generated by the narrow x-ray beam impinges on the reception area. In fact it is conceivable to maintain the x-ray source stationary and to move the flat ribbon cable transversely to the x-ray beam, but preferable is a movement of the x-ray source and the x-ray beam, respectively, upon quasi stationary arrangement of the flat ribbon cable in the transverse direction. It shall be understood that the flat ribbon cable can be moved in the longitudinal direction at the same time.

In order to achieve a spatial resolution which is as high as possible, the extension of the area of impingement of the x-ray beam on the flat ribbon cable in the transverse direction has to be made small. In order to do this, a collimator is preferably provided or an equipment for bringing the x-ray beam into focus. Both precautions are measures known by themselves in x-ray technology.

In order to obtain a high resolution on the one hand, and to let the detector get sufficient energy of the secondary radiation on the other hand, it is envisioned according to one form of realisation of the invention that the extension of the x-ray beam in the longitudinal direction of the flat ribbon cable has a significantly larger dimension than in the direction transverse to it.

It has already been mentioned that the edge position of the conductor paths can also be determined with the aid of such an arrangement, when it is operated in the scanning mode. According to one form of realisation of the invention, it is preferable that this takes place with the aid of an x-ray detector for the primary radiation, which is disposed on that side of the flat ribbon cable which is opposite to the x-ray source. Naturally, the intensity of the received x-ray radiation varies in dependence of whether the radiation penetrates the flat ribbon cable in the region of the conductor paths or in the region of the insulation. Thus, it is offhand possible to determine on which position the conductor paths are disposed, in relation to the width dimension of the flat ribbon cable. With the aid of such an arrangement it is also possible to determine the total thickness of the flat ribbon cable. The difference between the measured intensity in the region outside the flat ribbon cable and in the region of the insulation is a measure for the total thickness of the flat ribbon cable. Furthermore, it can be detected whether the insulation between adjacent conductor paths has a reduced thickness, e.g. is "contracted" by shrinkage.

The position of the conductor paths bears naturally on the side edges of the flat ribbon cable. With the aid of the described arrangement, the side edge can also be determined, in order to determine the remaining positions of the conductor paths and the portions between the conductor paths in relation to the same. It may be advantageous to provide a separate edge detector, with the aid of which the side edges of a flat ribbon cable may be determined accurately. In order to do this, a simple optical arrangement may be used. Such an edge detector also allows to compensate for side movements of the flat ribbon cable during the measurement, which would otherwise result in measurement errors.

When the flat ribbon cable is irradiated with an x-ray beam which is punctiform or line-like in the longitudinal direction of the flat ribbon cable, the reception area of the detector for the x-ray luminescence radiation can be realised to be large, as already mentioned. However, it is alternatively possible to direct a relatively generously sized x-ray beam onto the flat ribbon cable, and to keep the field of vision of the receiving detector small at the same time, i.e. to create the possibility that the detector scans the flat ribbon cable transversely to the running direction only in a punctiform or line-like manner. In such a case, the x-ray detector for the position determination of the conductor paths can be realised as a line detector.

The device according to the invention for executing the method according to the invention envisions an x-ray source which is attached on a suitable support. On the same support, the detector for x-ray luminescence may also be attached; preferably, an arrangement is provided such that the support can be moved transversely to the longitudinal extension or movement direction, respectively, of the flat ribbon cable, in order to scan the flat ribbon cable. When an x-ray detector is additionally provided on the opposing side, it is also synchronously moved along, especially in the case that it consists of one or several punctiform receivers. When the x-ray detector is realised as a line detector, however, which extends across the width of the cable, the line detector may remain stationary, when the x-ray source, together with the luminescence detector, moves transversely to the movement direction of the cable. When the cable is irradiated with the x-ray radiation in a generously sized manner, the x-ray source may be stationary, too, so that only the detector for the x-ray luminescence radiation performs a scanning movement transversely to the cable.

When x-ray source and x-ray luminescence detector are situated on one side of the flat ribbon cable and an arrangement which is impermeable for x-rays but excitable is provided on the opposite side of the flat ribbon cable, like a copper sheet or the like, e.g., then the wall thickness of the insulation above the conductor paths can be measured, as well as the total wall thickness of the insulation. The x-ray radiation stimulates a secondary radiation or luminescence in the copper sheet, which penetrates the insulation in the regions outside the conductor paths and is received by the luminescence detector in an attenuated state.

It is to be understood that an evaluation equipment is envisioned for the device according to the invention, by means of which the measuring signals of the detectors are evaluated, in order to determine the individual parameters of a flat ribbon cable.

BRIEF DESCRIPTION OF SEVERAL VIEWS OF THE DRAWINGS

The invention will be explained in more detail by means of a realisation example, which is represented in drawings.

DETAILED DESCRIPTION OF THE INVENTION

Figure 1:
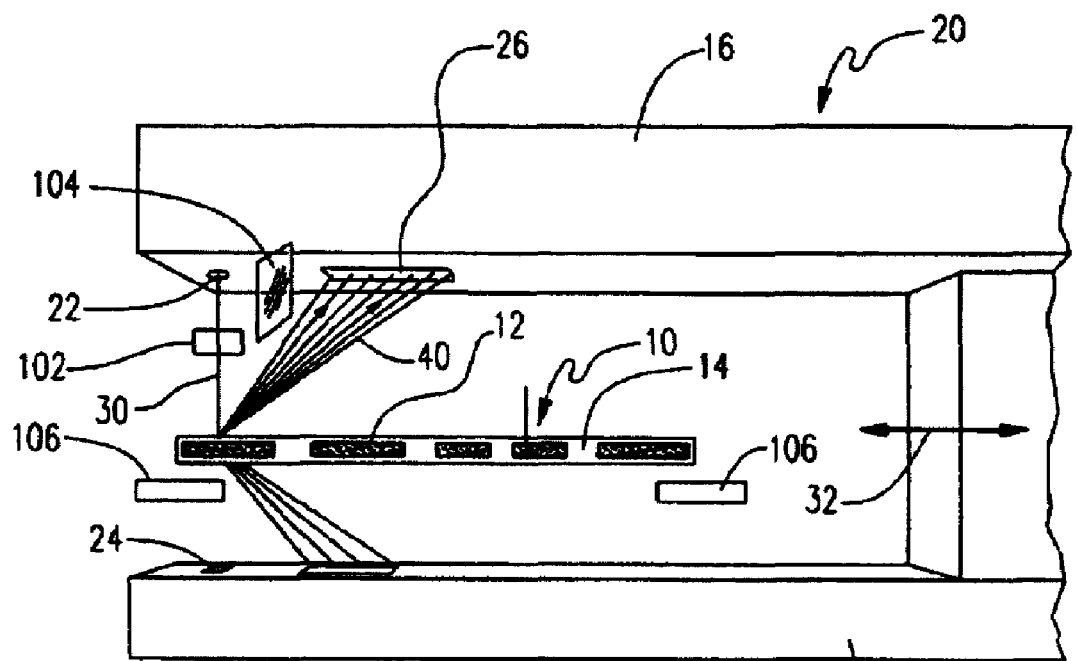
FIG. 1 shows schematically in perspective a device for the execution of the method according to the invention.

While this invention may be embodied in many different forms, there are described in detail herein a specific preferred embodiment of the invention. This description is an exemplification of the principles of the invention and is not intended to limit the invention to the particular embodiment illustrated In FIG. 1, a flat ribbon cable 10 is represented schematically in a cross section. It has five flat conductor paths 12, e.g. from copper, of different width, but equal thickness, which are arranged in certain distances from each other in a common plane. The arrangement of the flat conductors 12 is embedded in an insulation 14.

The flat ribbon cable 10 is conveyed perpendicularly to the drawing plane in its longitudinal direction by a not shown conveying equipment. It thereby moves between branches 16, 18 of an U-shaped support 20. In the upper branch 16, an x-ray source 22 is disposed. In the lower branch 18 an x-ray detector 24 is disposed opposite to the x-ray source 22. In the upper branch 16, an x-ray luminescence detector 26 is disposed in a distance to the x-ray source.

The x-ray source 22 is indicated only schematically. It generates an x-ray beam 30, which stands approximately perpendicularly on the plane of the flat ribbon cable 10. The x-ray beam 30 has a very small extension in the direction transverse to the flat ribbon cable 10, but is oblong in the longitudinal direction 12 of the flat ribbon cable, so that a line-like area of impingement results on the flat ribbon cable 10.

The x-ray detector 24 is equipped with a very small reception area (line-like). Several line-like sensors can also be envisioned. The reception area of the luminescence detector 26 is relatively large in relation to it.

During the measurement, the support 20 is moved to and fro in the direction of the double arrow 32 by a not shown driving equipment, so that the x-ray beam 30 oscillates across the entire width of the flat ribbon cable 20. This oscillating movement takes place continuously to and from, with constant forward movement of the flat ribbon cable 10.

The conductor paths 12 consist of metal, e.g. copper. Copper has a very small transmission factor with respect to x-ray radiation. Between the conductor paths 12, there is solely an insulation, which is permeable for the x-rays to a large extent. Thus, when the x-ray beam 30 moves across the width of the flat ribbon cable 10, a diagram according to FIG. 2 results, in which the intensity of the received x-ray beam is plotted in dependence of the width B of the flat ribbon cable 10. The pulses 34 generated by doing this represent the intensity in the spacings between adjacent conductor paths 12. In the region of the conductor paths 12, a relatively strong shielding takes place according to FIG. 2, the measured intensity is therefore low, about 25%. Thus, the edges 36 of the pulses accurately represent the position of the conductor paths 12 with respect to the side edges of the flat ribbon cable 10. When the zero point in the diagram corresponds to a side edge of the flat ribbon cable 10, a reference for the position of the edges 36, and with it for the position of the conductor paths 12 is obtained. Thus, with the aid of the described measuring device it can be determined whether the conductor paths 12 are disposed in the predetermined position in the production of the flat ribbon cable. It is to be understood that a suitable evaluation equipment has to be provided for the evaluation of the signals of the x-ray detector 24, which is not shown here.

The distance of the pulses 34 from the 100% intensity level corresponds to the total thickness wd1 of the insulation between the conductor paths.

When x-ray radiation impinges on e.g. metal, a secondary radiation is stimulated, which is emitted fromout the place of impingement. This is indicated in FIG. 1 at 40. The emitted radiation, an x-ray luminescence radiation, is on a significantly lower energy level than the x-ray beam 30. Consequently, the radiation 40 is absorbed in a certain degree by the insulation layer which is situated above the conductor paths 12. The detector 26 is equipped with a relatively large reception area, in order to convert the radiation feeble in energy into an utilisable signal.

Figure 3:
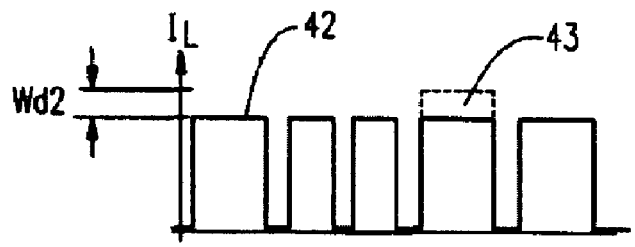
FIG. 3 shows a diagram from an x-ray luminescence measurement of the flat ribbon cable according to FIG. 1.

In FIG. 3, the intensity of this luminescence radiation is plotted over the width of the flat ribbon cable 10. Pulses 42 result in those regions in which a conductor path 12 is present, and pulse gaps between those pulses where there is mere insulation between the conductor paths 12, which generates no luminescence, of course. The distance of the pulses 42 from an intensity level 43 without insulation corresponds to the wall thickness wd2 of the insulation above a conductor path.

It is conceivable to omit the x-ray detector 24 and to work with the detector 26 only, when the position of the conductor paths is also to be determined, besides to the thickness of the insulation above the conductor paths 12. It is not possible, however, to determine the thickness of the flat ribbon cable 10 or its insulation, respectively, with the aid of such an arrangement.

Between the x-ray beam 30 and the detector 26, a shielding has to be provided, which makes for that no x-ray radiation impinges on the detector 26.

It is also possible to arrange a further detector, corresponding to detector 26, on the branch 18, like this is indicated in broken lines in FIG. 1, because the x-ray beam 30 generates also a secondary radiation after the penetration of the copper conductor on the lower side thereof, which emerges downward in the direction of the branch 18. In fact it is feebler than the radiation 40, but can also be measured, however. With it, the thickness of the insulation layer on the downside of the conductor paths 12 can be measured. The influence of the upper layer is negligible for this detector, because, as already mentioned, it is almost permeable for the x-ray beam 30. Naturally, the thickness of the lower insulation layer can also be determined by a second measuring arrangement, consisting of a second x-ray source and a luminescence radiation detector.

In order to create a restricted area of impingement of the x-ray beam 30 on the flat ribbon cable 10, suitable means like e.g. a collimator or an equipment for bringing the x-ray beam into focus can be provided. When such a ray zoning is not undertaken, it is also conceivable to provide an arrangement between the detector 26 and the flat ribbon cable, which makes it possible that the detector 26 views only one area element on the flat ribbon cable at a time, by setting a stop or the like before it.

In FIG. 1, the detector 26 is represented in a relatively large extension, transversely to the flat ribbon cable 10. However, it is preferable to provide the main extension of this detector 26 in the longitudinal direction of the flat ribbon cable 10. After all, it is also conceivable to use several such detectors for the x-ray luminescence, e.g. disposed in the longitudinal direction and in the transverse direction of the flat ribbon cable 10.

It is also conceivable to provide a detector row with a number of relatively small, narrowly recumbent sensor elements, alternatively to the line-shaped x-ray detector 24. Such a detector row would have to be arranged stationarily, while the x-ray source and/or detector 26 oscillate transversely across the flat ribbon cable.

Figure 2:
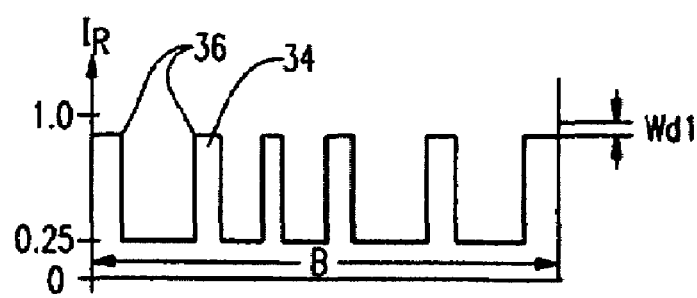
FIG. 2 shows a diagram of an x-ray transmission measurement of a flat ribbon cable.

It has been mentioned that e.g. with the aid of the diagram according to FIG. 2, the side edges of the flat ribbon cable 10 can be determined in the same manner like the side edges of the conductor paths 12. However, there is an uncertainty with respect to the side edges, insofar as the attenuation of the x-ray beam 30 by the insulation 14 is very faint. Therefore it can be advantageous to provide an additional edge detector instead of that, which works with an optical arrangement e.g., in order to get a better reference with respect to the position determination of the conductor paths 12.

Figure 4:
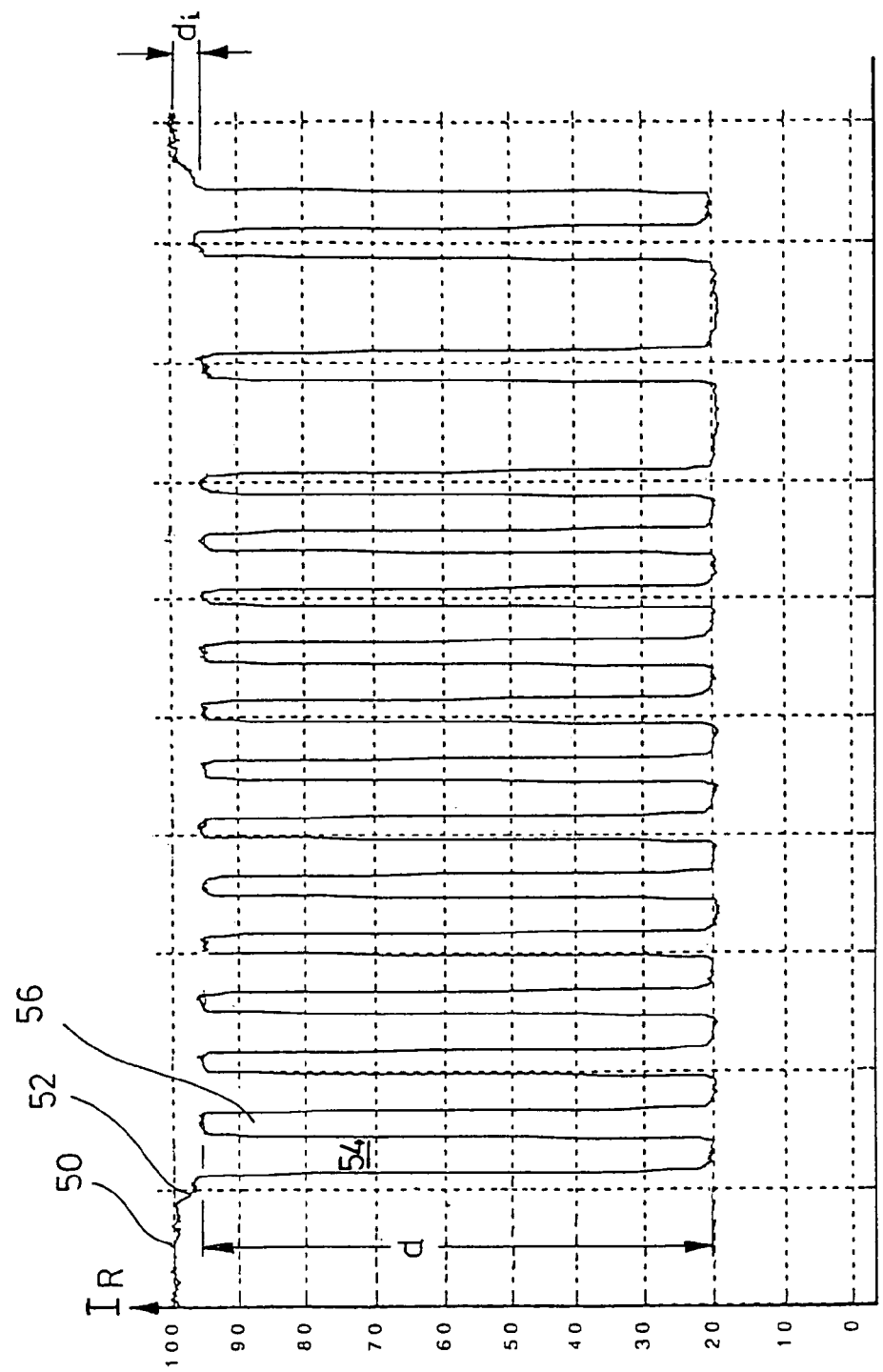
FIG. 4 shows a diagram similar to that of FIG. 2 with actual measurement values.

In FIG. 4 a diagram is represented which shows the measured intensity of the x-ray radiation at the position of detector 24. In so far, on principle there is coincidence with the diagram according to FIG. 2. It can be recognised that a flat ribbon cable has been scanned, which has a higher number of conductor paths than the flat ribbon cable 10 of FIG. 1. Furthermore, it can be recognised that the intensity of the received x-ray radiation in the region of mere insulation is not 100%, and also not zero in the region of the conductor paths. Thus, there is an influence of the insulation of the conductor paths, anyway. In the region 50 of the diagram after FIG. 4, the flat ribbon cable is outside the x-ray beam. It enters into the first insulation portion of the flat ribbon cable in the region 52 and is reduced to 20% of its intensity at 54 by the first conductor path. The next pulse 56 shows the build-up between adjacent conductor paths to an intensity of about 95%. The occurrences are repeated in the further scanning of the not shown flat ribbon cable. In this case, the distances between the pulses 56 indicate the spacings between adjacent conductor paths, and the edges of the pulses define the position of the conductor paths with respect to that one side edge which is defined as 52 in FIG. 4.

The difference between the pulses and the gaps 54 results in an intensity value d, which is a measure for the thickness of the conductor in the flat ribbon cable. Thus, it is possible to measure the thickness of the conductor with the described arrangement. The spacing between the 100% intensity according to 50 in FIG. 4 and the pulses 56 corresponds to the thickness di of the insulation. One recognises as well in FIG. 4 that the course of the pulses 56 is serrated in the individual pulses. It may also have a concave course, from which is deduced that the portions between the adjacent conductor paths are constricted, due to shrinkage of the material.

Figure 5:
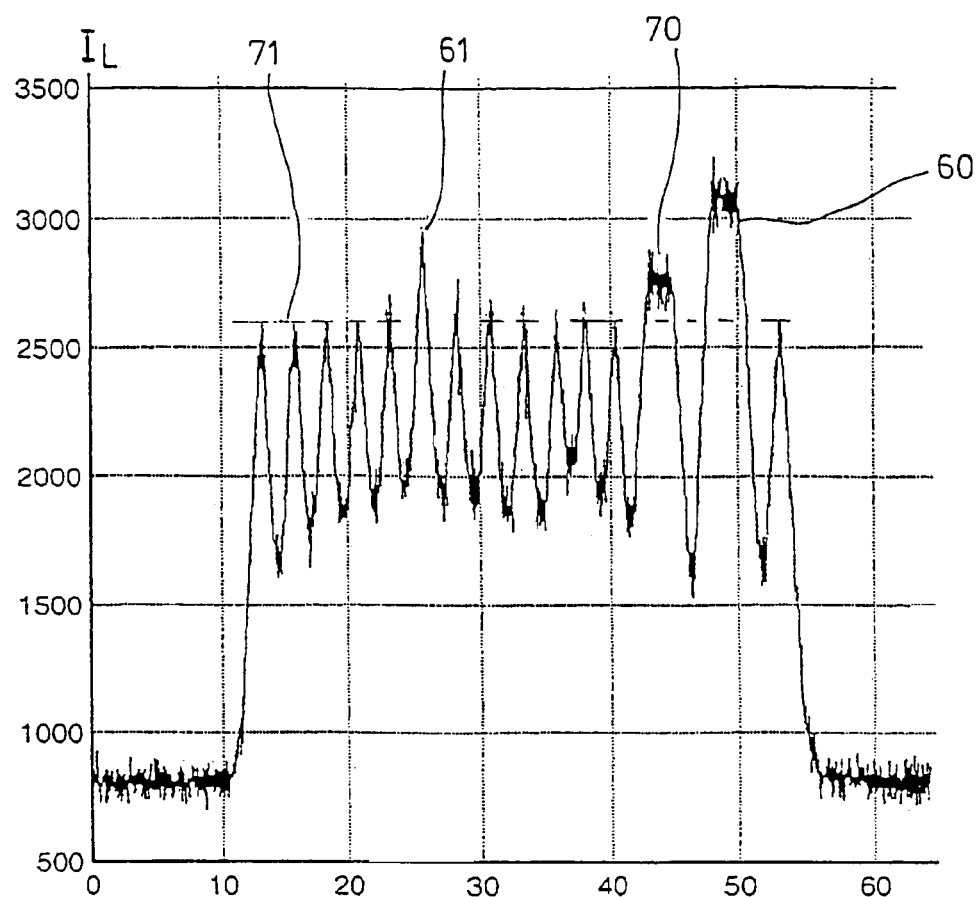
FIG. 5 shows a diagram similar to that of FIG. 3 with actual measurement values.

FIG. 5 represents a diagram for the course of the x-ray luminescence radiation in the scanning of the flat ribbon cable according to FIG. 4, which is measured with the detector 26 after FIG. 1, for instance. One can recognise that the individual pulses are not exactly situated on the same level. This is caused by insufficient focusing of the x-rays. In the case of the pulse 60 or 61, respectively, the insulation above the conductor had been removed. Thus, one clearly recognises that the intensity of the received x-ray luminescence radiation is significantly higher than at the conductor with insulation present, as indicated at 71 or 70. Thus, the intensity values of the luminescence radiation from the conductor paths give information about the thickness of the overlaying insulation.

It may be appropriate to ascertain a plurality of measurement values, which are generated by a plurality of scanning processes, in the not further discussed and not shown evaluation equipment, and to process them such that a mean value is determined, in order to compensate for statistical fluctuation, noise and measuring inaccuracies.

Figure 6:
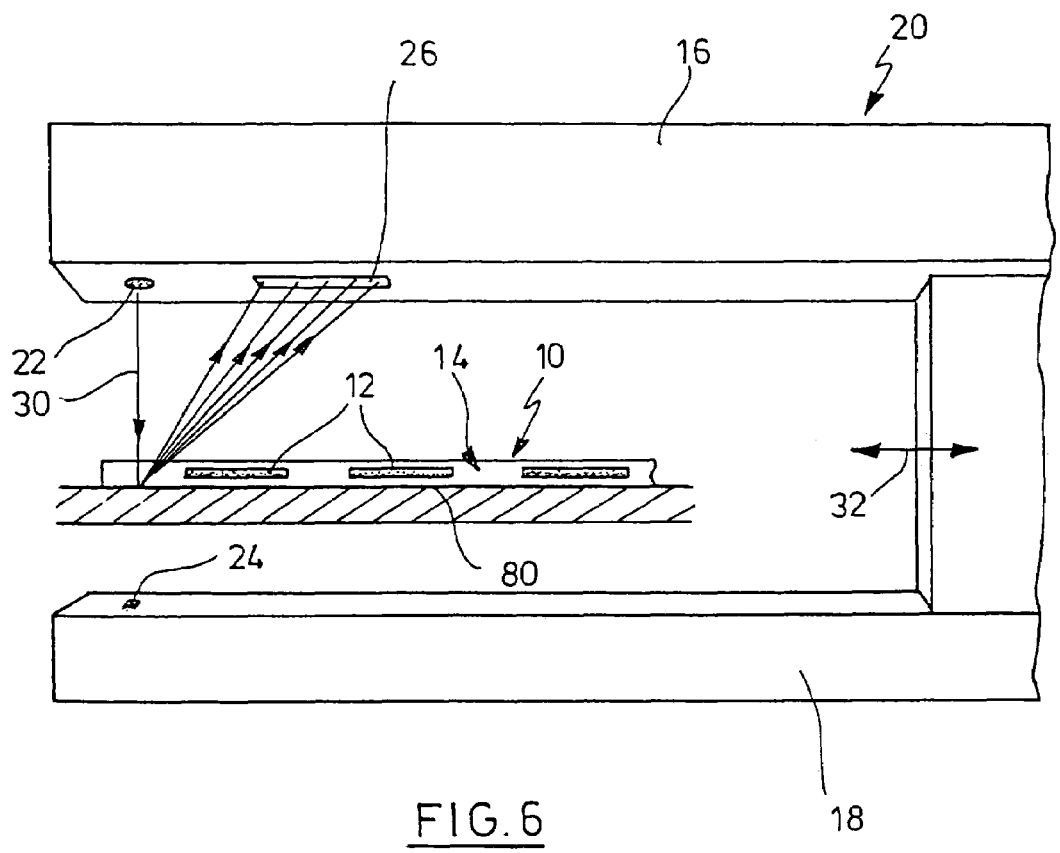
FIG. 6 shows an arrangement similar to FIG. 1, but in a modified measurement arrangement.
Figure 7:
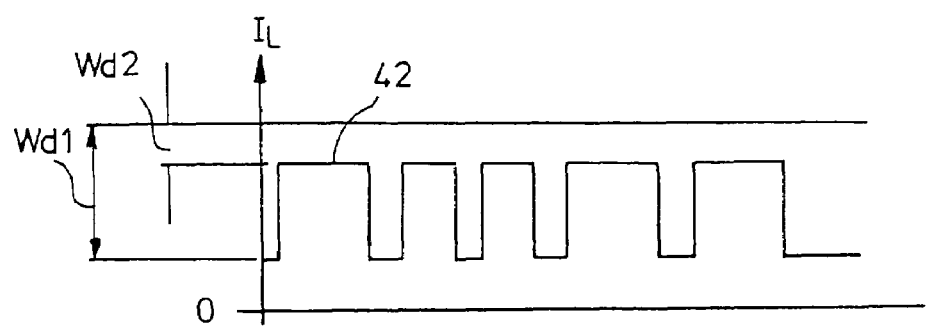
FIG. 7 shows a diagram from an x-ray luminescence measurement of the flat ribbon cable according to FIG. 6.

The embodiment according to FIG. 6 is similar to that according to FIG. 1, therefore equal parts are denoted with equal reference numerals. A copper sheet 80 is disposed below the flat ribbon cable 10. It has a thickness of 100 μm, e.g. Upon the x-ray irradiation of the flat ribbon cable, the copper sheet of small thickness 80 is stimulated to emit luminescence radiation on the one hand, and on the other hand the conductor paths 12 are also stimulated to emit luminescence radiation, as has been described above. Upon scanning, a diagram results as indicated in FIG. 7. The distance between the pulses 12 and a receiver input level without insulation yields the wall thickness of the insulation above the conductor paths. The distance between the pulse gaps and the described level yields the total thickness of the insulation between the conductor paths 12, which is denoted with wd1.

An x-ray detector, like the detector 24 after FIG. 1, is also provided. In fact, the sheet 80 attenuates the x-ray radiation, but its intensity below the sheet 80 is sufficient to stimulate the detector 24, in order to accomplish the determination of the position of the conductor paths, for instance.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method to determine the cross-sectional geometry of a flat ribbon cable, the flat ribbon cable having a longitudinal direction, an upper and a lower side and two edges, each edge having a position, and the flat ribbon cable comprising an insulation (14) and a plurality of parallel, metallic conductor paths (12) within the insulation, each having a width and being spaced from the edges of the flat ribbon cable and from each other, the insulation having a first thickness above and a second thickness below each conductor path, and a third thickness beyond the conductor paths, comprising the steps of:
   irradiating one side of the flat ribbon cable by means of an x-ray source with an x-ray beam which stimulates an emission of X-ray luminescence radiation from the metallic conductor paths with a predetermined intensity;
   shielding two detectors against the radiation of the x-ray source, one detector being provided on the same side of the flat ribbon cable as the x-ray source and the other detector being provided on the opposing side,
   measuring the intensity of the x-ray luminescence radiation and determining the first and the second thickness of the insulation,
   measuring the intensity of the x-ray radiation transmitted through the flat ribbon cable with a third detector placed on the opposing side of the flat ribbon cable as the x-ray source, and
   moving the x-ray beam and/or the third detector in a direction transverse to the longitudinal direction of the flat ribbon cable, so that the position of the edges of the cable and/or the spacings between each pair of adjacent conductor paths are determined from the intensity measured by the third detector.

2. The method according to claim 1, further wherein the x-ray source produces a beam directed to an area of impingement with an extension of the area of impingement on the flat ribbon cable which is small transversely to the longitudinal direction of the flat ribbon cable in relation to the width of the conductor paths and to the spacing between the conductor paths, and in that the x-ray beam is moved over the flat ribbon cable transversely to the longitudinal direction of the flat ribbon cable.

3. The method according to claim 2, wherein the x-ray beam is moved and the flat ribbon cable remains quasi stationary in the transverse direction, and the detectors are moved with the x-ray beam.

4. The method according to claim 1,
   further including the steps of directing the x-ray beam to an area of impingement with an extension of the area of impingement the flat ribbon cable and wherein the x-ray is brought into focus in a direction transverse to the longitudinal direction of the flat ribbon cable, and limiting the extension of the area of impingement by means of a collimator.

5. The method according to claim 1, further including the steps of:
providing each detector used to measure the x-ray luminescence radiation with a sensitive area, and
directing the x-ray beam to an area of impingement with an extension of the area of impingement on the flat ribbon cable, wherein the sensitive area of each detector is larger than the area of impingement on the flat ribbon cable.

6. The method according to claim 1, further including the step of determining the position of the side edges of the flat ribbon cable with the aid of a separate edge detector.

7. The method according to claim 1, further including the step of determining the spacing between the edges of the flat ribbon cable and the conductor path nearest to the edge from a measurement of the x-ray radiation transmitted through the flat ribbon cable.

8. The method according to claim 1, further including the step of determining the thickness of the insulation beyond the conductor paths from a measurement of the x-ray radiation transmitted through the flat ribbon cable.

9. The method according to claim 1, further including the step of determining the thickness of the flat ribbon cable in an area defined by a position of a conductor path, with this thickness being determined from a measurement of the x-ray radiation transmitted through the flat ribbon cable.

10. The method according to claim 1, characterized in that the position of the side edges of the flat ribbon cable is determined with the aid of a separate edge detector.

11. A device to determine the cross-sectional geometry of a flat ribbon cable, the flat ribbon cable having a longitudinal direction, an upper and a lower side and two edges, each edge having a position, and the flat ribbon cable comprising an insulation (14) and a plurality of parallel, metallic conductor paths (12) within the insulation, each having a width and being spaced from the edges of the flat ribbon cable and from each other, the insulation having a first thickness above and a second thickness below each conductor path, and a third thickness beyond the conductor paths, comprising:
an x-ray source with an x-ray beam is provided on the opposing side of the upper side of the flat ribbon cable, which stimulates an emission of x-ray luminescence radiation from the metallic conductor paths with a predetermined intensity;
two detectors, shielded against the radiation of the x-ray source, one placed on the same side of the flat ribbon cable as the x-ray source and another one on the opposing side, which measure the intensity of the x-ray luminescence radiation, so that the first and the second thickness of the insulation are determined;
a third detector is provided on the opposing side of the flat ribbon cable as the x-ray source which measures the intensity of the x-ray radiation transmitted through the flat ribbon cable, and
means are provided for moving the x ray beam and/or the third detector in a transverse direction to the longitudinal direction of the flat ribbon cable, so that the position of the edges of the cable and/or the spacings between each pair of adjacent conductor paths are determined from the intensity measured by the third detector.

12. The device according to claim 11, characterized in that the detector (26) is sensitive for x-ray luminescence and is disposed on the same side of the flat ribbon cable as is the x-ray source and further including a metallic plate or sheet (80) which disposed on the opposing side of the flat ribbon cable.

13. The device according to claim 11, characterized in that means are provided between the x-ray source and the flat ribbon cable so that a beam directed to an area of impingement is produced, with an extension of the area of impingement on the flat ribbon cable which is small transversely to the flat ribbon cable in relation to the width of the conductor paths and to the width of the insulating material between the conductor paths.

14. The device according to claim 13, characterized in that the means provided are formed by a collimator or by an equipment for bringing into focus the x-ray beam.

15. The device according to claim 14, wherein the x-ray beam has an area of impingement on the flat ribbon cable with an extension, characterized in that the collimator or the equipment for bringing into locus are formed such that the extension of the area of impingement in the longitudinal direction of the flat ribbon cable is larger than transverse to it.

16. The device according to claim 11, characterized in that the x-ray beam irradiates a larger area of the flat ribbon cable, each detector that measures the x-ray luminescence radiation has a sensitive area, and means are provided between these detectors and the flat ribbon cable through which the sensitive area of each detector receives only such luminescence radiation which origins from a small area, oriented transversely to the longitudinal direction of the flat ribbon cable.

17. The device according to claim 11, characterized in that a conveying equipment is provided which moves the flat ribbon cable forward in a first direction and that a support for the x-ray source is provided which moves transversely to the first direction in a second direction, and that a support for each detector is provided which moves synchronously with the support of the x-ray source.

18. The device according to claim 11, characterized in that the x-ray source and each detector that measure the luminescence radiation are attached to a common support, each detector having a sensitive area, the x-ray beam and each detector being formed such that the sensitive area of each detector receives only such x-ray luminescence radiation which, seen in a direction transverse to the longitudinal direction of the flat ribbon cable, origins from very narrow area portions of the flat ribbon cable at a time.

19. The device according to claim 11, characterized in that the detector that measures the x-ray radiation transmitted through the flat ribbon cable has a point-shaped reception area in a direction transversely to the longitudinal direction of the flat ribbon cable.

20. The device according to claim 11, characterized in that the detector that can measure the x-ray radiation transmitted through the flat ribbon cable a line sensor.

21. The device according to claim 11, characterized in that a separate edge detector is provided.

22. A method to determine the cross-sectional geometry of a flat ribbon cable, the flat ribbon cable having a longitudinal direction, an upper and a lower side and two edges, each edge having a position, and the flat ribbon cable comprising an insulation (14) and a plurality of parallel, metallic conductor paths (12) within the insulation, each having a width and being spaced from the edges of the flat ribbon cable and from each other; the insulation having a first thickness above and a second thickness below each conductor path, and a third thickness beyond the conductor paths, comprising the steps of:

placing a metallic sheet adjacent a surface of the flat ribbon cable;

irradiating the flat ribbon cable and the metallic sheet with an x-ray source with an x-ray beam, which is placed on the opposing side of the flat ribbon cable as the metallic sheet, which stimulates an emission of x-ray luminescence radiation from the metallic conductor paths and from the metallic sheet with a predetermined intensity;

placing a detector, shielded against the radiation of the x-ray source, on the same side of the flat ribbon cable as the x-ray source;

measuring the intensity of the x-ray luminescence radiation, and moving the x-ray beam and/or the detector in a direction transverse to the longitudinal direction of the flat ribbon cable, so that the first, second and/or third thickness of the insulation, and the position of the edges of the cable and/or the spacings between each pair of adjacent conductor paths are determined from the intensity measured by the detector.

23. A device to determine the cross-sectional geometry of a flat ribbon cable, the flat ribbon cable having a longitudinal direction, an upper and a lower side and two edges, each edge having a position, and the flat ribbon cable comprising an insulation (14) and a plurality of parallel, metallic conductor paths (12) within the insulation, each having a width and being spaced from the edges of the flat ribbon cable and from each other, the insulation having a first thickness above and a second thickness below each conductor path, and a third thickness beyond the conductor paths, comprising:

a metallic sheet is provided, placed below or above the flat ribbon cable, an x-ray source with an x-ray beam is provided on the opposing side of the flat ribbon cable as the metallic sheet which irradiates the flat ribbon cable and the metallic sheet, thereby stimulating an emission of x-ray luminescence radiation from the metallic conductor paths and from the metallic sheet with an intensity, a detector is provided, shielded against the irradiation of the x-ray source and placed on the same side of the flat ribbon cable as the x-ray source, which measures the intensity of the x-ray luminescence radiation, and means are provided to move the x-ray beam and/or the detector in transverse direction to the longitudinal direction of the cable, so that the first or the second thickness as well as the third thickness of the insulation, and the position of the edges of the cable and/or the spacings between each pair of adjacent conductor paths are determined from the intensity measured by the detector.

* * * * *